United States Patent
Gebhardt et al.

(10) Patent No.: US 6,907,786 B1
(45) Date of Patent: Jun. 21, 2005

(54) DEVICE FOR INJECTING ULTRASONIC WAVES INTO A MEDIUM

(75) Inventors: Wolfgang Gebhardt, Spiesen (DE); Rudolf Licht, Blieskustel (DE)

(73) Assignee: Fraunhofer-Gesellschaft zur Forderung der angewandten Forschung e.V., Munich (DE)

( * ) Notice: Subject to any disclaimer, the term of this patent is extended or adjusted under 35 U.S.C. 154(b) by 0 days.

(21) Appl. No.: 09/856,843

(22) PCT Filed: Dec. 17, 1999

(86) PCT No.: PCT/EP99/10094

§ 371 (c)(1),
(2), (4) Date: May 25, 2001

(87) PCT Pub. No.: WO00/35338

PCT Pub. Date: Jun. 22, 2000

(30) Foreign Application Priority Data

Dec. 17, 1998 (DE) ................................ 198 61 017

(51) Int. Cl.$^7$ ............................................ G01N 29/00
(52) U.S. Cl. ...................................................... 73/644
(58) Field of Search .......................... 73/571, 633, 634, 73/635, 636, 637, 638, 639, 671, 665, 861.18, 73/861.23, 644

(56) References Cited

U.S. PATENT DOCUMENTS

| | | | |
|---|---|---|---|
| 3,399,314 A | | 8/1968 | Philips |
| 4,033,178 A | * | 7/1977 | Holt et al. .................... 73/644 |
| 4,378,699 A | * | 4/1983 | Wickramasinghe .......... 73/606 |
| 4,454,764 A | * | 6/1984 | Sorenson ..................... 73/642 |
| 4,787,407 A | * | 11/1988 | Vogel ........................ 73/290 V |
| 4,944,186 A | * | 7/1990 | Dorr ............................ 73/644 |

FOREIGN PATENT DOCUMENTS

DE          1 095 021         12/1960

\* cited by examiner

*Primary Examiner*—Helen C. Kwok
(74) *Attorney, Agent, or Firm*—Antonelli, Terry, Stout & Kraus, LLP

(57) ABSTRACT

The invention is a device for coupling ultrasonic waves into a medium via a boundary surface, including at least one ultrasonic-wave transducer unit, which couples ultrasonic waves into the medium via a coupling medium provided between the ultrasonic-wave-generating unit and the boundary surface. The ultrasonic waves generated by the ultrasonic transducer unit are directed into a closed volume, which is provided with at least a first opening and a second opening. A flow of gas, ensures an overpressure inside the closed volume and simultaneously is the coupling medium. The flow of gas is directed into the interior of the volume through the first opening and exits the second opening which directly faces the boundary surface.

24 Claims, 1 Drawing Sheet

DEVICE FOR INJECTING ULTRASONIC WAVES INTO A MEDIUM

TECHNICAL FIELD

The present invention relates to a device for coupling ultrasonic waves into a medium via a boundary surface, having at least one ultrasonic transducer unit, which couples the ultrasonic waves into the medium via a coupling medium provided between the at least one ultrasonic transducer unit and the boundary surface.

STATE OF THE ART

Devices of the aforementioned type are employed for non-destructive examination of materials and, moreover, find widespread use in medicine for diagnosing inside the human body, for example physical examinations during pregnancy.

The interaction of ultrasound and preferably solid bodies is based, similar to light in glass, on absorption (weakening), reflection and refraction. Reflection and refraction occur at the boundary surface between two substances of different physical properties, e.g. at a boundary surface of a body. As these differences are often small, in particular in the case of composite materials, high sensitivity of the receiver device is a prerequisite by means of which the back reflected ultrasonic waves can be detected. Frequently ultrasound emitters and ultrasound receivers are integrated in one unit and are known as ultrasonic transducer systems. In order to be able to use an ultrasonic transducer both as an emitter and as a receiver, ultrasonic waves are emitted in short intervals and the reflected ultrasound is received in the pauses.

DESCRIPTION OF THE INVENTION

The present invention improves a device for coupling ultrasonic waves into a medium via a boundary surface, having at least one ultrasonic transducer unit which couples ultrasonic waves into the medium via a coupling medium provided between the at least one ultrasonic transducer unit and the boundary surface in such a manner that the degree of coupling with which the ultrasound is coupled into the medium, is distinctly raised. Moreover, the invention achieves close coupling between the at least one ultrasonic-wave transducer unit and the medium to be examined for better detection of the ultrasonic waves reflected at the medium.

With in air-coupled excitation of the ultrasonic waves, in which the air is utilized as the coupling medium, according to the present invention, a compressed air sliding shoe, is employed to decisively improve energy balance.

Air-coupled excitation of ultrasonic waves refers to the ultrasonic transducer unit generating ultrasonic waves in the air, with these ultrasonic waves striking the boundary surface of a solid body surface at a suited angle after passing through a long path and excite indirect waves (so-called density waves or shear waves or surface waves) running along the surface of the solid body, (so-called Rayleigh waves or creeping waves) in the medium in a solid body. In this way, various plate-wave modes can be excited even at plate-shaped materials.

The device of the invention has ultrasonic waves generated by the ultrasonic transducer unit which are directed into a closed volume provided with at least a first opening and a second opening. A flow of gas, which ensures that there is an overpressure inside the closed volume and simultaneously represents the coupling medium, is directed into the interior of the volume through the first opening. The second opening, through which the flow of gas coming from the volume exits, faces the boundary surface directly.

Preferably compressed air is introduced as the coupling medium into the interior of the closed volume, which is enclosed in a housing. The compressed air flows out through at least one opening on the side of the housing facing the boundary surface. Due to the selective outflow of the compressed air at the underside of the housing of the compressed-air sliding shoe, the sliding shoe is actually sucked to the boundary surface due to the so-called compressed hydrodynamic paradox, thereby yielding very close coupling between the housing and the boundary surface. This again results in, for the most part, a constant distance between the device and the boundary surface thereby improving measuring conditions considerably.

As an alternative to the hydrodynamic paradox effect, the intensity of the gas flow can be raised further in such a manner that a kind of air cushion is formed between the device and the boundary surface so that the entire device hovers over the boundary surface like a kind of hovercraft.

The main advantage of the closed volume, to which compressed-air is applied, inside the compressed-air sliding shoe, is that due to the pressure-dependent higher air density inside the housing, the ultrasonic waves can couple more effectively into the medium, which is preferably a solid body, via the boundary surface. Usually the pressure inside the compressed-air sliding shoe is approximately 10 times higher than in the surroundings. Thus, the ultrasonic waves can be coupled into the medium 10 times better.

The device of the invention couples ultrasonic waves preferably at those technical surfaces which, due to cleaning conditions or similar circumstances, cannot be directly contacted with a probe. With the device of the invention, ultrasonic waves can be coupled in a highly effectively manner to the boundary surface without physical contact and without complicated sealing technology for maintaining the air pressure inside the housing and inside the compressed air sliding shoe because the pressure conditions are set automatically as a result of the hydrodynamic paradox.

For further details, reference is made to the following preferred embodiments.

BRIEF DESCRIPTION OF THE DRAWINGS

The present invention is made more apparent in the following preferred embodiments described with reference to the accompanying drawings by way of example without the intention of limiting the scope or spirit of the inventive idea.

DESCRIPTION OF THE PREFERRED EMBODIMENTS

Figure 1:
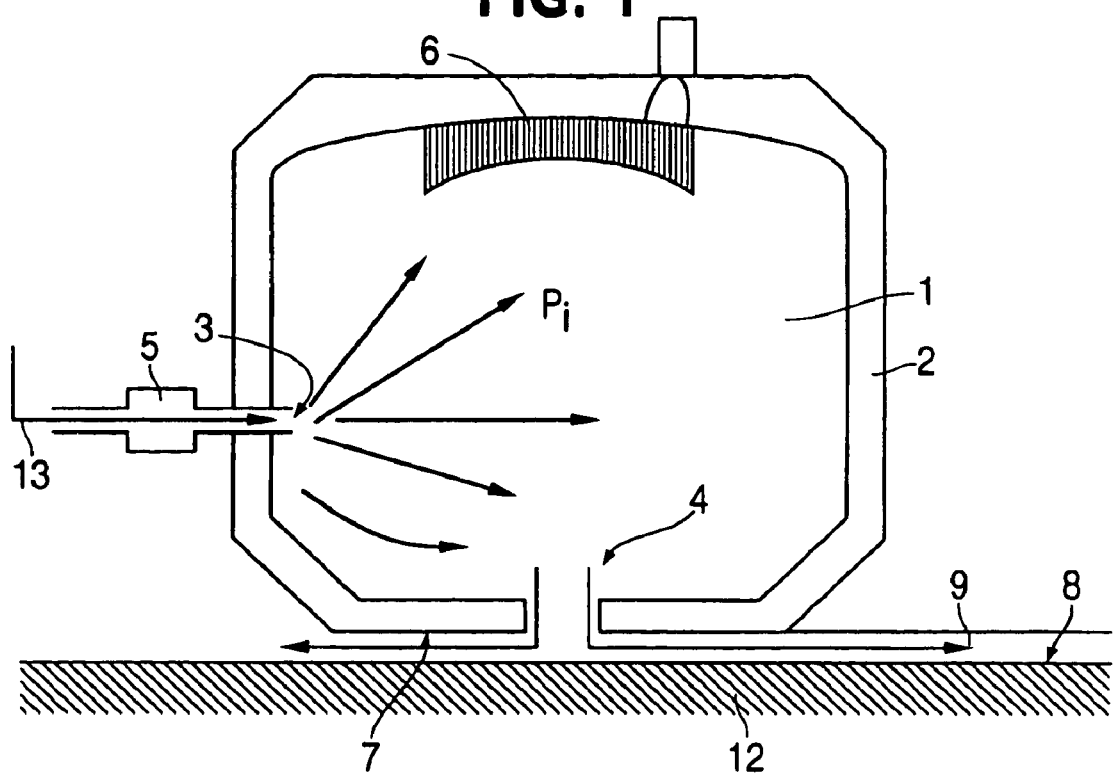
FIG. 1 is a cross section of an advantageous embodiment

In the simplest form of a preferred embodiment (FIG. 1), compressed air 13 flows into the closed volume 1, which is enclosed by a housing 2. The housing 2 is provided with two openings 3, 4. The compressed air flows into the interior of the housing 2 through opening 3 through a compressed-air line 5 attached thereto. The compressed-air escapes to the outside through the other opening 4. An ultrasonic transducer unit 6, preferably placed on the side facing opening 4, is provided inside the housing 2 in such a manner that the ultrasonic waves from the transducer are directed toward the opening 4. In this case, opening 4 also acts as an opening through which sound exits.

Preferably, delay-time-controlled stacked transducers are used as ultrasonic transducer units. Conventional transducers can also be built into the compressed-air sliding shoe. In particular for low frequency applications, the individual plates of the stacked transducers can be excited in phase. Conventional single oscillator transducers can, of course, also be used.

The compressed-air flow 9 flowing radially between the underside 7 of the housing and the solid body 12 being probed with ultrasonic waves has a surface 8 which generates a vacuum between the two surfaces which draws the compressed-air sliding shoe to the surface 8. The diminishing distance between the underside of the sliding shoe and the probe surface 8 raises flow velocity, which causes an increased contact force. Equilibrium sets in when the force of attraction generated by the radial flow equals the force of repulsion (caused by the pressure building up inside the sliding shoe). The width of the air gap between the underside of the sliding shoe and the probe surface and the amount of pressure inside the sliding shoe depends on the geometric design.

Figure 2:
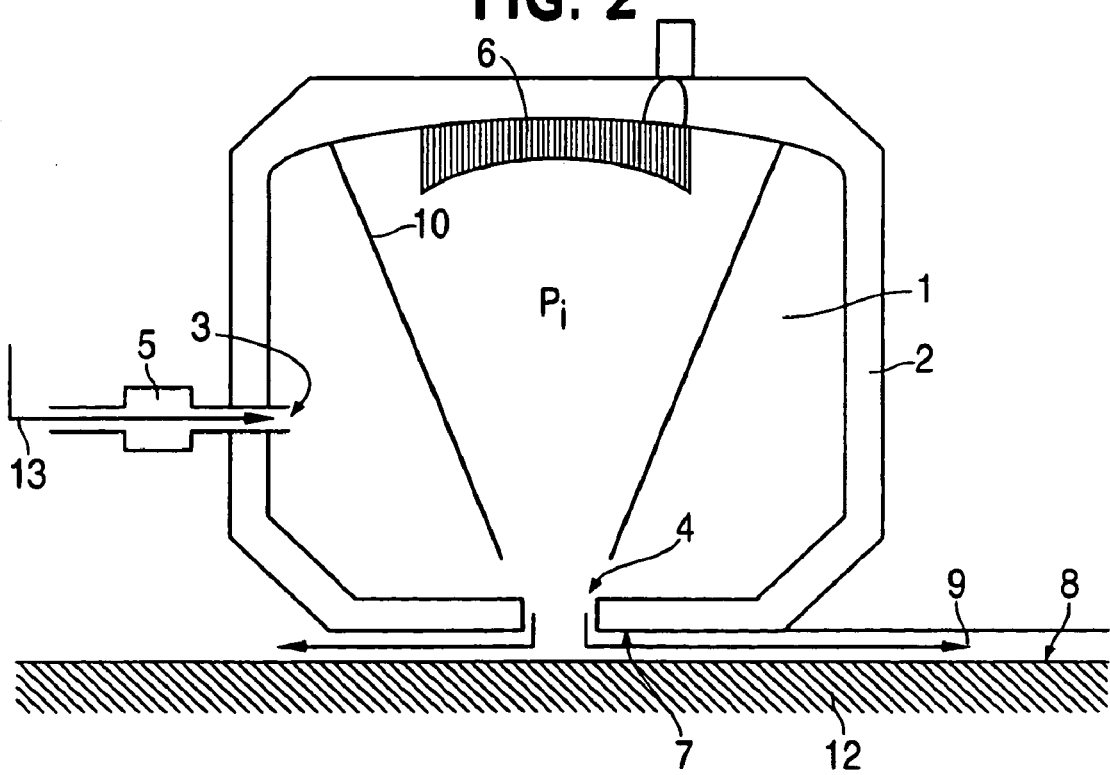
FIG. 2 is a cross section of an advantageous alternative embodiment.

However, the described simplest version of the compressed sliding shoe has certain drawbacks which are caused by gas-flow turbulences inside the housing 2, which in particular, cause the occurrence of disturbing fluctuations in the shape and the amplitude of the ultrasonic pulses inside the housing 2. In order to reduce these disturbances, sound-conducting means 10 are built into the interior of the housing 2 in order to deflect and/or concentrate the ultrasonic waves toward the sound-exit opening 4. The purpose of the sound-conducting means 10 is, in particular, to separate the spatial zone through which the ultrasonic waves pass and a spatial zone in which the gas flow is introduced into the housing. In FIG. 2, a funnel insert, which concentrates the ultrasonic waves coming from the ultrasonic transducer unit in the direction of the sound-exit opening 4, is provided as the sounding-conducting means 10.

The interaction volume between the turbulent compressed air and sound is therefore very much limited which reduces turbulent effects accordingly. Fundamentally instead of a funnel, all built-in elements such as baffle plates, hole filters etc. can be used which contribute to a laminating or calming the air flow. Of course, any other gas (e.g. $CO_2$) can be employed instead of compressed air.

Moreover, the sound exit opening and other compressed-air openings can be disposed on the housing separated from each other.

Depending on the application, the ultrasonic transducer unit 6 can be built into the housing perpendicular to the surface 8 or slanted to generate oblique ultrasonic waves. If transmission and reception are realized with two ultrasonic transducers, they can be built into separate sliding shoes or into a common sliding shoe. In the latter case, the two transducers can have separate sound-exit openings with separate baffles for suppressing turbulences or common sound-exit openings with a common baffle for suppressing turbulences. The geometric arrangement (slanted position, spacing) is adapted depending on the application (testing thick components or thin components, exciting spatial waves, surface waves or plate waves).

LIST OF REFERENCE NUMBERS

1 closed volume
2 housing
3,4 openings
5 compressed-air line
6 ultrasonic transducer unit
7 underside
8 boundary surface, probe surface
9 compressed-air flow
10 sound-conducting means

What is claimed is:

1. A device for coupling ultrasonic waves into a solid body to be ultrasonically probed via a boundary surface located outside a closed volume comprising:
    at least one ultrasonic-wave transducer unit, which couples ultrasonic waves into the solid body via a gaseous coupling medium provided between the at least one ultrasonic-wave transducer unit and the boundary surface, wherein the ultrasonic waves generated by the at least one ultrasonic-wave transducer unit are directed into the closed volume, which is provided with at least a first opening and a second opening;
    the closed volume being bordered by a housing, in which the at least one ultrasonic-wave transducer unit is contained, including a housing surface spaced from the boundary surface which defines and extends outward from the second opening to define a channel between the housing surface and the boundary surface; and
    a source of gas providing a flow of gas producing an overpressure inside the closed volume which is directed into an interior of the closed volume through the first opening, and which exits the closed volume through the second opening which directly faces the boundary surface and flows through the channel outward from the second opening while contacting the housing and the boundary surface; and wherein
    the flow of gas passes through the second opening facing the boundary surface and flows between an upper side of the housing and the boundary surface and the boundary surface and upper surface extends radially relative to the second opening to define the channel, and a vacuum draws the housing toward the boundary surface to create a gas cushion in the channel of a thickness at which a force of attraction is created by the vacuum and a force of repulsion present due to a mass impulse of the flow of gas between the housing and the boundary surface are in equilibrium.

2. The device according to claim 1, wherein the closed volume is bordered by a housing in which the at least one ultrasonic-wave transducer unit is contained to cause the ultrasonic waves to be directed at the second opening directly facing the boundary surface.

3. The device according to claim 1, wherein the flow of gas is air.

4. The device according to claim 3, wherein the flow of air is compressed air.

5. The device according to claim 4, comprising a compressed air line connected to the first opening.

6. The device according to claim 1, comprising sound conducting means for coupling ultrasonic waves inside the closed volume toward and through the second opening.

7. The device according to claim 3, comprising sound conducting means for coupling ultrasonic waves inside the closed volume toward and through the second opening.

8. The device according to claim 4, comprising sound conducting means for coupling ultrasonic waves inside the closed volume toward and through the second opening.

9. The device according to claim 5, comprising sound conducting means for coupling ultrasonic waves inside the closed volume toward and through the second opening.

10. The device according to claim 6, wherein the sound conducting means separates a first spatial zone inside the closed volume, in which ultrasonic waves propagate without interference with the flow of gas, and a second spatial zone in which the gas flow is directed.

11. The device according to claim 6, wherein the sound conducting means comprises a funnel which guides the ultrasonic waves from the at least one ultrasonic-wave transducer unit to the second opening without being impeded by the flow of gas.

12. The device according to claim 1, wherein the at least one ultrasonic-wave transducer unit comprises a transmitter and a receiver.

13. The device in accordance with claim 1 wherein:
the channel is of substantially uniform spacing measured between the housing and the boundary surface.

14. The device in accordance with claim 2 wherein:
the channel is of substantially uniform spacing measured between the housing and the boundary surface.

15. The device in accordance with claim 3 wherein:
the channel is of substantially uniform spacing measured between the housing and the boundary surface.

16. The device in accordance with claim 4 wherein:
the channel is of substantially uniform spacing measured between the housing and the boundary surface.

17. The device in accordance with claim 5 wherein:
the channel is of substantially uniform spacing measured between the housing and the boundary surface.

18. The device in accordance with claim 6 wherein:
the channel is of substantially uniform spacing measured between the housing and the boundary surface.

19. The device in accordance with claim 7 wherein:
the channel is of substantially uniform spacing measured between the housing and boundary surface.

20. The device in accordance with claim 8 wherein:
the channel is of substantially uniform spacing measured between the housing and the boundary surface.

21. The device in accordance with claim 9 wherein:
the channel is of substantially uniform spacing measured between the housing and the boundary surface.

22. The device in accordance with claim 10 wherein:
the channel is of substantially uniform spacing measured between the housing and the boundary surface.

23. The device in accordance with claim 11 wherein:
the channel is of substantially uniform spacing measured between the housing and the boundary surface.

24. The device in accordance with claim 12 wherein:
the channel is of substantially uniform spacing measured between the housing and the boundary surface.

\* \* \* \* \*